(12) United States Patent
Reiner

(10) Patent No.: US 10,614,388 B2
(45) Date of Patent: *Apr. 7, 2020

(54) METHOD AND APPARATUS FOR REAL-TIME MEASUREMENT AND ANALYSIS OF OCCUPATIONAL STRESS AND FATIGUE AND PERFORMANCE OUTCOME PREDICTIONS

(71) Applicant: Bruce Reiner, Berlin, MD (US)

(72) Inventor: Bruce Reiner, Berlin, MD (US)

( * ) Notice: Subject to any disclaimer, the term of this patent is extended or adjusted under 35 U.S.C. 154(b) by 314 days.

This patent is subject to a terminal disclaimer.

(21) Appl. No.: 15/164,081

(22) Filed: May 25, 2016

(65) Prior Publication Data

US 2016/0267405 A1    Sep. 15, 2016

Related U.S. Application Data

(63) Continuation of application No. 13/537,976, filed on Jun. 29, 2012, now Pat. No. 9,380,978.

(Continued)

(51) Int. Cl.
  *G06Q 10/06*    (2012.01)
  *A61B 5/00*    (2006.01)
  (Continued)

(52) U.S. Cl.
  CPC .......... *G06Q 10/06* (2013.01); *A61B 5/0022* (2013.01); *A61B 5/021* (2013.01); *A61B 5/165* (2013.01); *A61B 5/4884* (2013.01); *G06Q 50/22* (2013.01); *A61B 5/0002* (2013.01); *A61B 5/18* (2013.01); *A61B 2503/20* (2013.01);
  (Continued)

(58) Field of Classification Search
  None
  See application file for complete search history.

(56) References Cited

U.S. PATENT DOCUMENTS 4,683,891 A * 8/1987 Cornellier .......... A61B 5/0533
                                                              600/301
5,016,635 A   5/1991 Graupe
              (Continued)

FOREIGN PATENT DOCUMENTS

WO    2007/145900 A2    12/2007
WO    2010/051037 A1    5/2010

OTHER PUBLICATIONS

Krupinski et al., Measurement of Visual Strain in Radiologists, Acad Radiol. Aug. 2009; 16(8): 947-950.
(Continued)

*Primary Examiner* — Carl H Layno
*Assistant Examiner* — Manolis Pahakis
(74) *Attorney, Agent, or Firm* — Edwards Neils LLC; Jean C. Edwards, Esq.

(57) ABSTRACT

The present invention relates to a method and apparatus to objectively measure stress and fatigue using measurement tools, record stress and fatigue related data in a standardized database, create automated prompts and alerts based upon pre-defined stress and fatigue thresholds (which are derived based upon individual end-user and task performance), provide a number of interventions (which can be preferentially selected by the individual end-user), create data-driven best practice guidelines though meta-analysis of the database, and provide an objective tool for comparative technology assessment.

19 Claims, 6 Drawing Sheets

Related U.S. Application Data

(60) Provisional application No. 61/457,891, filed on Jun. 29, 2011, provisional application No. 61/649,723, filed on May 21, 2012.

(51) Int. Cl.
*A61B 5/021* (2006.01)
*A61B 5/16* (2006.01)
*G06Q 50/22* (2018.01)
*A61B 5/18* (2006.01)

(52) U.S. Cl.
CPC ....... *A61B 2503/22* (2013.01); *A61B 2503/24* (2013.01); *G06Q 10/0639* (2013.01)

(56) References Cited

U.S. PATENT DOCUMENTS

| | | | |
|---|---|---|---|
| 5,305,238 A | 4/1994 | Starr, III et al. | |
| 5,471,382 A | 11/1995 | Tallman et al. | |
| 5,682,882 A | 11/1997 | Lieberman | |
| 5,813,993 A | 9/1998 | Kaplan et al. | |
| 5,878,156 A | 3/1999 | Okumura | |
| 5,888,173 A | 3/1999 | Singhal | |
| 6,070,098 A | 5/2000 | Moore-Ede et al. | |
| 6,104,296 A | 8/2000 | Yasushi et al. | |
| 6,107,922 A | 8/2000 | Bryuzgin | |
| 6,126,596 A | 10/2000 | Freedman | |
| 6,173,260 B1 | 1/2001 | Slaney | |
| 6,246,779 B1 | 6/2001 | Fukui et al. | |
| 6,259,655 B1 | 7/2001 | Witort | |
| 6,416,472 B1 | 7/2002 | Cady et al. | |
| 6,511,424 B1 | 1/2003 | Moore-Ede et al. | |
| 6,530,884 B2 | 3/2003 | Balkin et al. | |
| 6,542,081 B2 | 4/2003 | Torch | |
| 6,575,902 B1 | 6/2003 | Burton | |
| 6,673,026 B2 | 1/2004 | Pozos et al. | |
| 6,701,231 B1 | 3/2004 | Borugian | |
| 6,718,235 B1 | 4/2004 | Borugian | |
| 6,731,307 B1 | 5/2004 | Strubbe et al. | |
| 6,873,714 B2 | 3/2005 | Witt et al. | |
| 6,927,694 B1 | 8/2005 | Smith et al. | |
| 7,027,621 B1 | 4/2006 | Prokoski | |
| 7,043,056 B2 | 5/2006 | Edwards et al. | |
| 7,081,095 B2 | 7/2006 | Lynn et al. | |
| 7,171,277 B2 | 1/2007 | Engleson et al. | |
| 7,202,793 B2 | 4/2007 | Grace et al. | |
| 7,233,312 B2 | 6/2007 | Stern et al. | |
| 7,349,782 B2 | 3/2008 | Churchill et al. | |
| 7,593,549 B2 | 9/2009 | Reiner | |
| 7,593,861 B2 | 9/2009 | Morrel-Samuels | |
| 7,607,079 B2 | 10/2009 | Reiner | |
| 7,849,115 B2 | 12/2010 | Reiner | |
| 7,974,961 B2 | 7/2011 | Barbarek | |
| 8,081,165 B2 | 12/2011 | Reiner | |
| 8,096,946 B2 | 1/2012 | Burton | |
| 8,117,549 B2 | 2/2012 | Reiner | |
| 8,214,227 B2 | 7/2012 | Patterson et al. | |
| 8,249,892 B2 | 8/2012 | Reiner | |
| 8,540,629 B2 | 9/2013 | Jain et al. | |
| 8,926,531 B2 | 1/2015 | Sone et al. | |
| 2001/0007055 A1 | 7/2001 | Fukuda | |
| 2003/0078505 A1 | 4/2003 | Kim et al. | |
| 2004/0078231 A1 | 4/2004 | Wilkes et al. | |
| 2004/0210548 A1 | 10/2004 | Ketcherside, Jr. et al. | |
| 2005/0148894 A1 | 7/2005 | Misczynski et al. | |
| 2005/0154264 A1 | 7/2005 | Lecompte et al. | |
| 2006/0274145 A1 | 12/2006 | Reiner | |
| 2007/0017531 A1 | 1/2007 | Large | |
| 2007/0282912 A1 | 12/2007 | Reiner | |
| 2008/0188777 A1 | 8/2008 | Bedziouk et al. | |
| 2008/0221396 A1 | 9/2008 | Garces et al. | |
| 2008/0312963 A1 | 12/2008 | Reiner | |
| 2009/0018867 A1 | 1/2009 | Reiner | |
| 2010/0145720 A1 | 6/2010 | Reiner | |
| 2011/0041077 A1 | 2/2011 | Reiner | |
| 2011/0216181 A1* | 9/2011 | Yoda | A61B 5/1103 348/78 |
| 2011/0218815 A1 | 9/2011 | Reiner | |
| 2011/0245624 A1 | 10/2011 | Ballegaard | |
| 2011/0270123 A1 | 11/2011 | Reiner | |
| 2012/0025993 A1* | 2/2012 | Akiyama | A61B 5/18 340/576 |
| 2012/0059669 A1 | 3/2012 | Whittenburg et al. | |
| 2012/0078063 A1 | 3/2012 | Moore-Ede | |
| 2012/0289793 A1 | 11/2012 | Jain et al. | |
| 2012/0319869 A1* | 12/2012 | Dorfmann | A61B 5/18 340/945 |
| 2013/0185168 A1 | 7/2013 | Lee et al. | |
| 2014/0072192 A1 | 3/2014 | Reiner | |
| 2014/0358585 A1 | 12/2014 | Reiner | |

OTHER PUBLICATIONS

SR Research Ltd., EyeLink@ User Manual version 1.3.0, 2007.
Non-Final Office Action issued in U.S. Appl. No. 13/537,976 dated Oct. 25, 2013.
Final Office Action issued in U.S. Appl. No. 13/537,976 dated Sep. 12, 2014.
Notice of Allowance issued in U.S. Appl. No. 13/537,976 dated Oct. 25, 2013 dated Apr. 29, 2016.

* cited by examiner

METHOD AND APPARATUS FOR REAL-TIME MEASUREMENT AND ANALYSIS OF OCCUPATIONAL STRESS AND FATIGUE AND PERFORMANCE OUTCOME PREDICTIONS

CROSS-REFERENCE TO RELATED APPLICATIONS

The present invention is a continuation of U.S. patent application Ser. No. 13/537,976, filed Jun. 29, 2012, issued as U.S. Pat. No. 9,380,978, which claims the benefit of U.S. Provisional Patent Application No. 61/457,891, filed Jun. 29, 2011, and 61/649,723, filed May 21, 2012, the contents of all of which are herein incorporated by reference in their entirety.

BACKGROUND OF THE INVENTION

1. Field of the Invention

The present invention relates to a method and apparatus to objectively measure stress and fatigue, record stress and fatigue related data in a standardized database, create automated prompts and alerts based upon pre-defined stress and fatigue thresholds (which are derived based upon individual end-user and task performance), provide a number of interventions (which can be preferentially selected by the individual end-user), create data-driven best practice guidelines though meta-analysis of the database, and provide an objective tool for comparative technology assessment.

2. Description of the Related Art

Stress and fatigue are commonly encountered challenges within contemporary medical practice and affect all healthcare professionals to varying degrees. Over the past few years, a number of factors have served to increase stress and fatigue among healthcare professionals including (but not limited to) reduced reimbursements (with a resulting emphasis on increased productivity and workflow), increased scrutiny on quality and safety, changing regulations, and the digitization of medical practice.

In current medical practice, healthcare professionals are to a large degree left to their own devices. If and when a physician is tired, stressed, or fatigued, they must not only identify the concern but also unilaterally take action to avoid error. This is often impractical given workload demands, time constraints, and lack of availability of a readily available replacement. As a result, the physician often continues work, with the potential to alter workflow, operational efficiency, quality of performance, or patient safety. In addition, a culture of perseverance often exists, which encourages healthcare professionals to "work through" the stress/fatigue. The only way to correctly ascertain how this impacts clinical outcomes is through prospective data collection and analysis, which is currently unavailable given the lack of supporting technology. Current workflow analysis is largely performed on a "macro" and retrospective level, where individual healthcare workers and departments are evaluated on the basis of cumulative productivity (e.g., annual exams or procedures) or operational efficiencies (e.g., patient waiting times or backlogs). Since increased emphasis is placed on productivity and operational efficiency, minimal effort is made to identify causative factors of stress and fatigue and potential remedies.

A number of landmark publications have been issued from the Institute of Medicine which has highlighted the unexpectedly high frequency of medical errors and occupational stress/fatigue among healthcare professionals. These publications have cited the relatively high frequency of medical errors resulting in avoidable deaths, magnifying the importance of operator vigilance, concentration, and computerized decision support. Thus, technology has been a double-edged sword for healthcare providers. On one hand it has dramatically improved the quality and accessibility of data, while on the other hand it has created heightened expectations on the part of consumers and increased stress on the part of service providers, which is highly variable in accordance with the individual end-user's technology proclivity, education/training, and occupational demands.

In addition, the analysis of data in medical practice is complex and comes in multiple forms; including textual, numerical, graphical, and imaging data. Healthcare professionals must be able to review this multi-disciplinary data and make rapid and well-informed decisions. Any form of visual fatigue can potentially impair data recognition and analysis, while cognitive fatigue can lead to faulty and/or delayed decision-making.

The digitization of medical practice has profoundly changed the manner in which medical data is recorded, transmitted, accessed, and analyzed. While this digitization has improved data accessibility, it has also presented healthcare professionals with less "down time" in which they can take a break, decompress, and relax from high pressure occupational demands. The ubiquitous nature of data within the electronic medical record and other healthcare information system technologies creates continuous demand for continuous workflow, which in turn can serve as a stress and fatigue multiplier. The end result is that data intensive occupations which rely on instantaneous decision-making with the potential for catastrophic results are particularly vulnerable to stress and fatigue induced error.

An additional factor contributing to occupational stress and fatigue is sleep deprivation, which can be of particular concern in occupations and workers during evening and night time shifts, in which natural circadian rhythms are disrupted. A large number of reports have cited concerns over stress and fatigue within medical practice and the exacerbation caused by sleep deprivation. The criticality of the problem is best illustrated in critically ill and emergent patient populations, where a small time delay or oversight can lead to the difference between life and death.

An additional deficiency of current technology is the "one size fits all" approach, which essentially treats all end-users as a homogeneous population. Differences in occupation, education, personality, computer proclivity, and sensory/motor skills are largely ignored. Instead, end-users are forced to adapt to the technology, rather than the technology being adaptive to their unique needs.

Occupational stress and fatigue is not solely the domain of healthcare professionals and is also commonly found within other occupations exposed to high pressure productivity/workflow demands, increased quality and safety concerns, and prolonged periods of time interacting with a computer. These include (but are not limited to) the transportation, defense, engineering, and software industries. A great deal of work has been dedicated to airline pilots and traffic controllers, who are prone to occupational stress and fatigue, with the potential for instantaneous catastrophe, in the event of an oversight or error.

Thus, a proactive technology which can account for inter-user variability and introduce accommodative measures has the potential to improve performance, while also reducing or minimizing occupational stress and fatigue, would be advantageous. Further, a technology which can potentially diagnose stress and fatigue, and intervene in the end-user's performance in real-time, could provide tremendous benefit on a number of levels including improved workflow, safety, quality, and morale.

SUMMARY OF THE INVENTION

The present invention relates to a method and apparatus to objectively measure stress and fatigue, record stress and fatigue related data in a standardized database, create automated prompts and alerts based upon pre-defined stress and fatigue thresholds (which are derived based upon individual end-user and task performance), provide a number of interventions (which can be preferentially selected by the individual end-user), create data-driven best practice guidelines though meta-analysis of the database, and provide an objective tool for comparative technology assessment.

The present invention seeks to expand the functionality of a technology currently used in widespread use, with the combined goals of reducing occupational stress/fatigue, while simultaneously improving the economics and quality of healthcare deliverables. The stress/fatigue measurement tools for integration in the method and apparatus of the present invention include devices for measuring visual, physiologic, and cognitive forms of stress/fatigue (i.e., blood pressure monitors, speech analysis, etc.).

The present invention provides real-time standardized measurement of occupational stress and fatigue; creates a standardized database for stress/fatigue, workflow, quality performance, and clinical outcomes data; creates an end-user profiling system (and peer reference groups), which would take into account a number of specific attributes and characteristics of the individual end-user; creates a standardized measure for task complexity; creates customizable stress/fatigue interventions commensurate with individual end-user style preferences and observed stress/fatigue analytics; and provides a technology assessment tool, which provides a standardized mechanism for correlating stress/fatigue measures with task performance, workflow, and specific technology in use.

Thus, the present invention provides a methodology and apparatus for creating a technology which can be customized to the unique needs and preferences of individual end-users, while also providing objective data-driven "best practice" guidelines, based upon historical end-user and context-specific performance.

While the present invention is applicable to a diverse number of industry applications, like engineering, software, pilots, etc., the medical profession is used for illustrative purposes.

Thus, has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to a method and apparatus to objectively measure stress and fatigue, record stress and fatigue related data in a standardized database, create automated prompts and alerts based upon pre-defined stress and fatigue thresholds (which are derived based upon individual end-user and task performance), provide a number of interventions (which can be preferentially selected by the individual end-user), create data-driven best practice guidelines though meta-analysis of the database, and provide an objective tool for comparative technology assessment.

The present invention seeks to expand the functionality of a technology currently used in widespread use, with the combined goals of reducing occupational stress/fatigue, while simultaneously improving the economics and quality of healthcare deliverables. The stress/fatigue measurement tools for integration in the method and apparatus of the present invention include devices for measuring visual, physiologic, and cognitive forms of stress/fatigue (i.e., blood pressure monitors, speech analysis, etc.).

Figure 1:
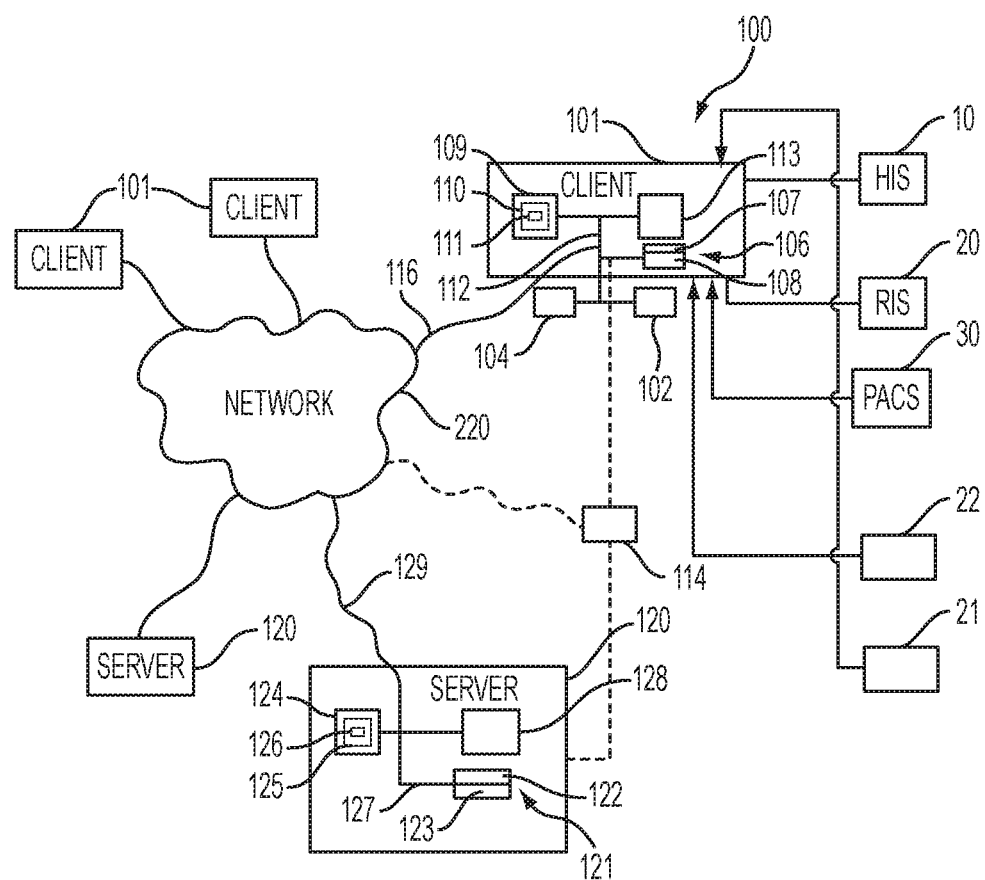
FIG. 1 is a schematic diagram which shows the overall components of the apparatus of the present invention.

According to one embodiment of the invention illustrated in FIG. 1, an apparatus for measuring data on a user's stress/fatigue, and which can analyze the data, may be implemented using the system 100. In a medical application, the system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a Picture Archiving and Communication System (PACS) 30, and/or other systems. In the medical application, the system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

In other applications, the system 100 would be designed to interface with other systems, such as an air traffic control system (in cases where the user is a pilot or air traffic controller), etc.

In all applications, the system 100 is connected to a measurement tool 22, which includes any or all devices that measures the visual, physiologic, and cognitive forms of stress/fatigue, such as eye tracking systems, blood pressure monitors, heart monitors, breathing monitors, speech recognition/analysis systems, etc.

According to one embodiment, bi-directional communication between the system 100 of the present invention and the information systems, such as the HIS 10, RIS 20, and PACS 30, etc., as well as the measurement tool 22, may be enabled to allow the system 100 to retrieve and/or provide information from/to these systems. According to one embodiment of the invention, bi-directional communication between the system 100 of the present invention and the other systems 30, 22 etc., allows the system 100 to update information that is stored on the information systems. According to one embodiment of the invention, bi-directional communication between the system 100 of the present invention and the other systems allows the system 100 to generate desired reports and/or other information.

The system 100 of the present invention includes a client computer 101, such as a personal computer (PC), which may or may not be interfaced or integrated with an information system (i.e., PACS 30) and the measurement tool 22. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the information system (i.e., PACS 30 and Electronic Medical Report (EMR)).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101. According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the information systems (i.e., HIS 10, RIS 20, PACS 30 etc.), or other external devices (i.e., measurement device 22, or medical equipment such as a radiographic device) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment. Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other non-transitory computer-readable media, such as secondary storage devices, like hard disks, floppy disks, CD-ROM, or other forms of ROM or RAM either currently known or later developed. Further, although specific components of the system have been described, one skilled in the art will appreciate that the system suitable for use with the methods and systems of the present invention may contain additional or different components.

The present invention includes a combination of external measurement tools 22 (i.e., sensors and components), and potentially other information or other systems, connected to a computer system 101, the combination which is designed to objectively measure stress and fatigue in an end-user, record the end-user's stress and fatigue-related data in a standardized database 113, 114, 128 etc., of the computer system(s) 101, 121, create automated prompts and alerts to the end-user based upon pre-defined stress and fatigue thresholds (which are derived based upon individual end-user and task performance), provide a number of interventions (which can be preferentially selected by the individual end-user), create data-driven best practice guidelines though meta-analysis of the database 113, 114, 128, and provide an objective tool for comparative technology assessment.

Generally, the present invention includes the following components: 1) a stress and fatigue measurement tool 22; 2) a standardized database 113, 114, 128 which records, tracks, and analyzes stress and fatigue data from the measurement tool(s) 22 in real time, along with individual end-user workflow, quality performance measures, and clinical outcomes; 3) an end-user profiling system provided by the program 110, which provides a mechanism to stratify individual end-users in accordance with a number of individual variables, which can influence stress and fatigue data; 4) a task performance analysis performed by the program 110, which provides an historical and objective, data-driven measure of task complexity; 5) a stress and fatigue interventional device and/or program 110, which provides end-user and task-specific options for stress/fatigue reduction; and 6) a technology assessment tool provided by the program 110, which provides technology-specific stress and fatigue measures, along with corresponding workflow and task performance data. Note that the above components may be used individually or in any number or combination.

In an exemplary embodiment, a radiologist in the current working environment and using available technology, interprets a number of medical imaging examinations during the course of a given workday, but without any measures of interventions related to stress and fatigue, and thus, without recording or analyzing any related data. However, using the present invention, a number of new technologies are introduced into the workflow, which includes (but are not limited to: imaging modalities (e.g., CT), information systems technologies (e.g., PACS, EMR), image processing software (e.g., MPR), and clinical decision support software (e.g., CAD). Technology components incorporated into the invention include the following: 1) sleep quality assessment; 2) stress assessment; 3) fatigue measurement, 4) end-user profile; and 5) task complexity scoring.

Taking the first technology component, sleep assessment can be measured by measurement tools 22, in a number of ways, including by external sensors (e.g., Sleep Scan, Sleep Image System), physiologic metrics (e.g., saliva evening cortisol, blood IGF-1 levels), and self-reported questionnaires (e.g., Pittsburgh Sleep Quality Index (PSQI), sleep efficiency). While any one of these assessment tools can be integrated into the system 100 to longitudinally track and analyze sleep quality, in this example, the PSQI is well accepted in the scientific community, is freely available, and brief, which makes it an ideal candidate for inclusion in the invention.

Regardless of the technology employed to measure sleep quality, standardized data is recorded by the measurement tool 22, and recorded into the master Stress/Fatigue Database (SFD) 113, 114, 128 of the system 100, which provides for program 110 real-time analysis of data, which can be correlated with baseline and historical end-user specific data stored in the database 113, 114, 128.

With respect to the second component, occupational stress assessment can be measured by measurement tool 22, on the end-user using a variety of available self-assessment survey instruments including the Job Stress Survey, Perceived Stress Scale, and Visual Analogue Scale. In addition to these stress assessment tools, subjective stress levels can be performed by the end-user, inputted into the database 113, 114, 128 of the system 100, and periodically monitored for changes by the program 110 during the course of the work shift, to assess interval changes over time, relative to the patient baseline. This provides a methodology to combine baseline and dynamic changes in stress, which can be correlated by the program 110 with objective measures of fatigue.

With respect to the third component, fatigue can be measured by measurement tool 22, using visual, physiologic, and cognitive assessment tools, which can be integrated into the system 100 of the present invention in isolation or combination, depending upon the occupation of the end-user, task being performed by the end-user, and available technology. Common measures of visual fatigue in the end-user include accommodation, dark vergence, and measures of blink rate and eyelid levels. Physiologic measures of fatigue of the end-user can be performed using readily available affective measuring tools 22 including heart rate, blood pressure, and galvanic skin response monitoring, which are continuously recorded by the program 110 in the database 113, 113, 128, allowing for the program's 110 rapid and immediate detection of interval change. Cognitive measures of fatigue include mathematical task, vigilance tasks, and repetitive reaction time tasks, which can be periodically introduced into the user's workflow by the program 110.

Commercially available measurement tools 22 (i.e., heart and blood pressure monitors, skin sensors, etc.) can be used for recording these measurements, and combined with the analytical program 110 of the present invention, can determine interval change relative to end-user and context-specific baselines (i.e., measuring stress, fatigue, etc.). Depending upon task complexity and quality performance of the individual end-user, the pre-defined threshold for 'acceptable" levels can be adjusted and stored in the database 113, 114, 128 for comparison with measured values.

Thus, in the present example of a radiologist, a radiologist interpreting a chest radiograph for evaluation of pneumonia (low complexity task) may be allowed to continue working given a fatigue measure by measurement tool 22 which exceeds baseline by 20% as determined by the program 110, whereas the same radiologist tasked with interpretation of a brain MRI for seizures (high complexity task) may be required by the program 110 to discontinue or modify workflow for the same given fatigue measurement. At the same time, in comparing two radiologists for the same task (e.g., CT angiography of the chest for aneurysm detection), one radiologist may have historically poorer quality assessment (QA) scores relative to the other radiologist. As a result, the "acceptable" fatigue threshold for the radiologist with lower QA scores would differ from that of the radiologist with higher QA scores. This illustrates the dynamic and customizable manner in which the technology of the present invention can be utilized.

The fourth component—end-user profiling—is an important and integral component of the program 110 of the present invention, for the program 110 provides an objective methodology for classifying end-user differences in accordance with a number of variables which affect a given individual's baseline, and dynamic stress and fatigue levels. Those variables include 1) demographics, 2) education and training, 3) work experience, 4) personality, 5) emotional state, 6) sensory and motor skills, and 7) intelligence. Through longitudinal analysis of the stress/fatigue database (SFD) 113, 114, 128 by the program 110, a classification schema can be derived which categorizes each individual end-user's propensity for stress/fatigue in accordance with the occupation, task complexity, technology being used, environmental factors, and external (i.e., not work-related) factors.

In one example, a technologist has a profile which categorizes him as "low stress", which in turn correlates with his historical stress/fatigue measures, which can be (graphically) tracked by the program 110 over time. Based upon the technologist's specific profile and historical data, a stress/fatigue variability measure can be derived by the program 110, which predicts the degree of stress/fatigue variation which is observed during the course of a given work shift. Whenever excessive variability is determined by the program 110 based upon inputs into the database 113, 114, 128, a more detailed analysis is instituted by the program 110 to identify the causative factors and attempt to intervene.

In this particular example, the historical stress/fatigue variability (SFV) for the user is +/−5-10% in accordance with the time of day and task complexity. As a result of this specific technologist's profile and corresponding data in the SFD, an automated prompt (i.e., alarm, email, text, etc.) is provided by the program 110 whenever measured fatigue levels reach 8% above baseline. When the prompt is generated at the local level (which in this example, takes place at the imaging modality workstation (i.e., radiographic device 21) at which the technologist is working), receipt acknowledgement must be obtained by the program 110 (i.e., using Biometrics in accordance with U.S. Pat. No. 7,593,549, to Reiner, which is herein incorporated by reference in its entirety), that documents that the recipient has viewed the data and is aware of the abnormal fatigue levels. If the pre-determined threshold of 10% is subsequently reached, a mandated alert is sent by the program 110 by electronic means (i.e., alarm, email, text, fax, etc.) which forces the technologist to act based upon the following options:

a) Stop working and take a break, with selection of one of the many stress-reduction options which have been customized by the program 110 to the specific needs and preferences of the end-user.

b) Continue working, but switch to tasks of lesser complexity, as determined by analysis of the data in the database 113, 114, 128, technology in use, and the specific end-user's profile, by the program 110.

c) Continue work (as-is) in an uninterrupted fashion, with an explanation inputted by the user into the database 113, 114, 128, as to why an alternative (and preferred) option has been overridden.

d) Select an alternative workflow pathway (while continuing with the same task), by utilizing computer-generated workflow options offered by the program 110, associated with decreased stress/fatigue (e.g., automated workflow templates).

If, for example, the technologist was to select option b) (continue working, switching to tasks of lesser complexity), the program 110 would provide a list of tasks to choose from, while automatically transferring the ongoing tasks to another technologist. While the technologist continues working at these tasks of lesser complexity, continuous stress/fatigue monitoring is provided by the program 110 with periodic real-time feedback provided to the technologist. Once the measured fatigue levels reach lesser levels which are determined to be within pre-determined "safe" levels by the program 110, the program 110 alerts the technologist that he/she is cleared for continuation of all tasks, with the corresponding fatigue measures provided.

In the example, in the event that the end-user selects the option to continue work as-is, and override the recommendations of the program 110, an automated prompt (i.e., email, text, alarm, alert etc.) is sent to a supervisor and quality control personnel by the program 110, in accordance with the a predetermined escalation pathway. This provides a documented trail of all abnormal stress/fatigue measures and ensuing actions taken by the user, as recorded by the program 110 to the database 113, 114, 128. Based upon institutional policy, established guidelines, and clinical outcomes stored in the database 113, 114, 128, the end-user who chooses to override the recommendations may be subject to disciplinary actions or remedial education, as instigated by the program 110. The end goal is to maximize quality, safety, and productivity in a manner which minimizes stress/fatigue, while utilizing technology and data to its fullest extent.

In another example, another technologist within the same institution and performing the same type of tasks, may have the program 110 call for different data-generated actions based upon that technologist's profile. Thus, the technologist in question would be subject to greater variability in fatigue measures by the program 110, with routine variability of +/−15-20%. As a result of these differences in end-user profile analysis by the program 110, the program 110 generates a warning prompt (i.e., alarm, email, text, etc.) would not be activated until a measure of 18% above baseline is taken by the sensor tools, and recorded into the database. In this example, the technologist of interest has a history of quality and/or safety deficiencies once high fatigue measures have been measured. As a result, the program 110 may adjust the options to ensure that continuous work by the technologist is not an option (i.e., partial or complete shutdown of the computer system 100, radiographic device 21, etc.), along with incorporation of additional checks and balances (e.g., requisite oversight by a senior technologist).

With respect to the fifth and final component, task complexity, due to the fact that tasks being performed are associated with different levels of complexity, and in turn can generate disproportionate degrees of stress and fatigue for the operator or user, it is important for the program 110 to incorporate task complexity into the overall analysis. For a radiologist tasked with interpretation of different imaging examinations, lower complexity examinations can be re-routed to his/her queue during periods of measured or anticipated higher stress/fatigue. In this way, workflow becomes dynamically integrated with the program 110, based upon the individual end-user profile, measured stress/fatigue levels, and task complexity. If a particular radiologist has a pre-defined tendency to measure higher fatigue levels at certain times of the workday, the program 110 may automatically adjust workflow accordingly, by directing lower complex tasks during the time periods of concern. On the other hand, if the radiologist of interest reports poor quality sleep or increased anxiety (e.g., health or family concerns, emotional issues), the program 110 can automatically make workflow adjustments to compensate. A tool such as the Productivity Workflow Index (see U.S. patent application Ser. No. 12/137,926 to Reiner, filed Jun. 12, 2008, the contents of which are herein incorporated by reference in their entirety), can be directly integrated into the program 110 to provide objective user and context-specific measures of task complexity to assist with the process.

Intervention options are an important component of the program 110 of the present invention and provide an effective mechanism to compensate for abnormal fatigue and stress measures. The various types of intervention options are, for example, 1) environmental (changing temperature, light, ventilation), 2) exercise (aerobic and anaerobic, ocular), 3) relaxation techniques (breathing, yoga, nap, meditation etc.), 4) dietary (herbal supplements, pharmacologic agents), 5) massage, 6) aromatherapy, 7) (on-line) games and puzzles, 8) music, and 9) programs etc. that instigate laughter. However, many more under direct control of the system 100, or the end-user, or both, can be utilized.

The intervention options can be customized by the program 110 in accordance with individual end-user preferences, the severity and type of measurement abnormalities, and the specific task being performed. These interventional techniques can be incorporated into each individual end-user's profile by the program 110, so that the user's specific preferences are automatically presented by the program 110 at the time of an abnormal fatigue measurement being taken by the measurement tool(s) 22, and recorded by the program 110. In addition to each individual end-user's preferences, the program 110 can store interventional preferences of similar profile users along with the ensuing results. This provides an effective data-driven record of cause and effect, which assists selection of interventional techniques based upon prior success under similar circumstances.

As an example, a surgeon who has been sleep deprived may experience abnormally high fatigue measures and be forced to opt for intervention in order to reduce fatigue levels to acceptable levels before proceeding with his/her work. The surgeon may select an option provided by the program 110, for music intervention, and select from a list of available music options. Upon selection of a specific musical piece, the program 110 can search the database 113, 114, 128, and perform an analysis of the intervention success of that specific type of music, in accordance with the stress/fatigue measures recorded, end-user profile, and tasks being performed. Based upon this analysis, the program 110 can provide the end-user with an estimate of time required before the intervention has achieved the desired effect of reducing stress/fatigue levels to the baseline level, allowing the end-user to proceed with the requisite task. In performing this analysis, the program 110 may identify several alternative music options which have higher success rates, in terms of the degree of fatigue reduction and time required to achieve the pre-determined reduction required. These options, along with corresponding data analyses can be presented to the surgeon by the program 110, for review. The surgeon can in turn elect to stick with his/her original choice, or opt for one of the alternative options with a higher success rate. This essentially provides end-users with the ability to manually select intervention options of their choosing or allow the program 110 to search the database to provide a list of options with high degree of user and context-specific success. This can be performed on individual or grouped options, so that the program 110 may provide an end-user with a combination of interventions (e.g., music+relaxation technique) which has proven to be of high success in tandem with one another.

The historical record of each individual end-user's fatigue and intervention measures can be reviewed and analyzed by the program 110 to identify trends and opportunities for improvement. As changes are made in workflow, technology in use, or tasks being performed, each individual end-user's data can be reviewed by the program 110 and correlated with similar end-users. This provides comparative analysis to identify "best practice" trends among end-users with similar profiles and tasks, with the ability for the program 110 to analyze those end-users with the highest performance analytics (as determined by quality, productivity, safety, and stress/fatigue measures).

In operation, the following provides an exemplary method, using the example of a radiologist tasked with the interpretation of medical imaging exams. With minor modification, this workflow and invention functionality can be applied to any healthcare practitioner (e.g., surgeon, nurse, technologist) or workers in non-medical fields which utilize computers for prolonged periods of time (e.g., pilots, air traffic controllers, architect, engineer, software developer). Even a routine task such as everyday driving, may utilize the proposed technology, with the realization that sleep deprived, impaired, and/or long distance drivers are prone to lapses in concentration and/or diminished reaction times, which can lead to increased risk for accidents and injury. While the present invention does not intend to directly measure chemical impairment due to alcohol and/or drug use since the present invention operates in real-time, the resulting physiologic, visual, and cognitive impairment can be recognized by the program 110 and proactively acted upon using the invention and associated data. The program 110 can analyze the longitudinal database to identify trending analysis and specific times and dates in which abnormal fatigue measures were recorded, which in turn could correlate, for example, with abnormal substance use (e.g., alcohol, prescription/illicit drugs). As noted below, the analysis of the database 113, 114, 128 by the program 110 provides an important role in administrative review and quality assurance (QA), irrespective of the end-user, occupation, and tasks being performed.

Figure 2A:
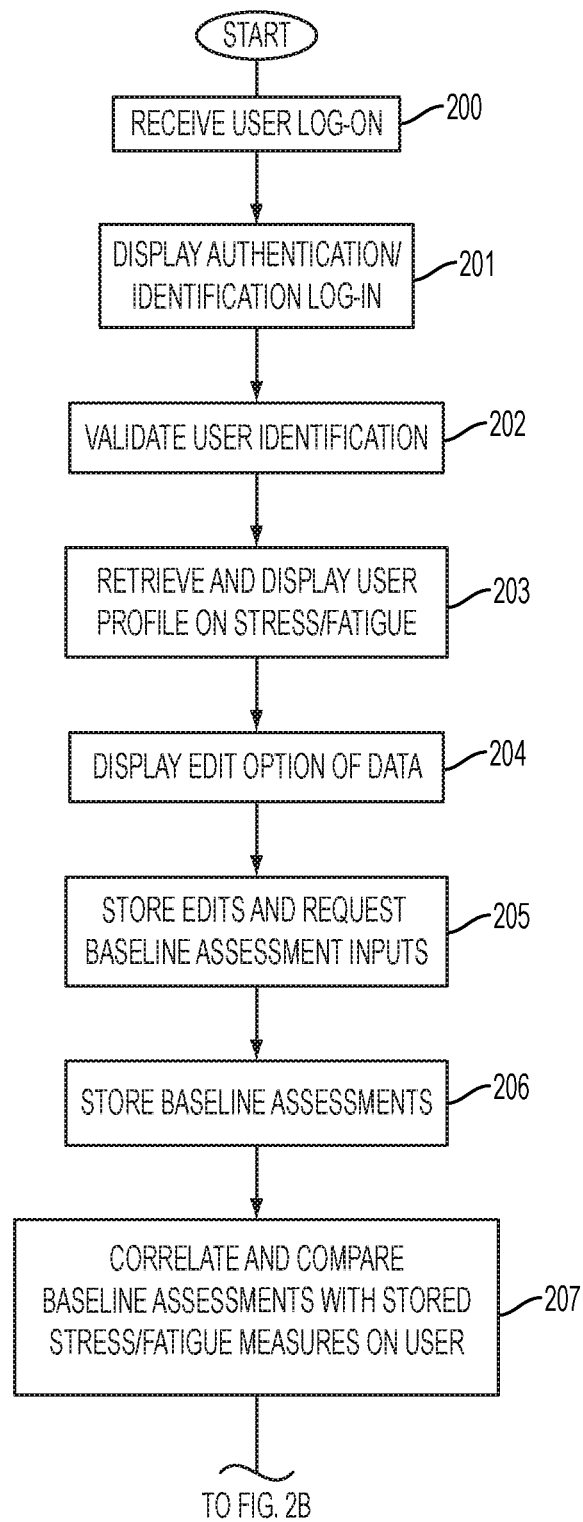
FIGS. 2A-2C are flowcharts showing steps in the method of the present invention.

In step 200, of FIG. 2A, the program 110 receives the end-user's log-on to the system 100, including any external devices (i.e., measurement tool 22, external equipment 21, etc.).

In step 201, the program 110 displays an authentication/identification log-in using biometrics, for example.

In step 202, the program 110 receives and validates the user's identification against the stored information.

In step 203, the program 110 retrieves the user's specific profile on stress/fatigue from the database, and the end-user's analytics, and presents the user with his/her customized profile and statistical analysis for review.

In step 204, the program 110 provides an option for the end-user to query any of the details provides, or edit any of the data stored in the database 113, 114, 128, which includes the following: a) end-user classification schema (e.g., occupation, emotional stress, baseline sleep quality); b) tasks performed; c) customizable preferences (e.g., fatigue/workflow intervention options); d) threshold criteria and notification options; and e) analytics (e.g., types of analytics routinely performed, feedback options, recommendations for improvement).

In step 205, once any details are provided or edits received and stored in the database 113, 114, 128, the program 110 prompts the end-user for baseline assessments on a) sleep quality, and b) stress (emotional state), prior to the user beginning any specific tasks.

In step 206, the program 110 receives and stores the user's inputs on baseline assessments. The baseline stress/fatigue measurements obtained include, but are not limited to, visual, physiologic, and cognitive measurements using tools 22.

In step 207, the program 110 correlates the baseline fatigue and stress measures with the data stored on the end-user in the database 113, 114, 128.

In step 208, the program 110 presents the end-user with default workflow options, based upon the user's historical use, profile, and sleep/stress/fatigue inputs. In particular, the program 110 generates a (graphical) display of baseline/historical data with statistical predictions and recommendations for workflow, rest periods, task assignments, and supporting technologies.

In step 209, the end-user is presented with the option on the display 102 to modify the program 110 generated recommendations or accept "as is".

In step 210, if desired, the end-user can edit/modify the workflow options including (but not limited to) type of tasks to be performed, task complexity, frequency of fatigue measurements. The program 110 then returns the user to step 208, where the edited workflow, predictions and recommendations are again displayed.

In step 211, the program 110 begins the workflow based upon the inputted baseline measurements, historical analysis of stress/fatigue inputs, and end-user inputs.

Figure 2B:
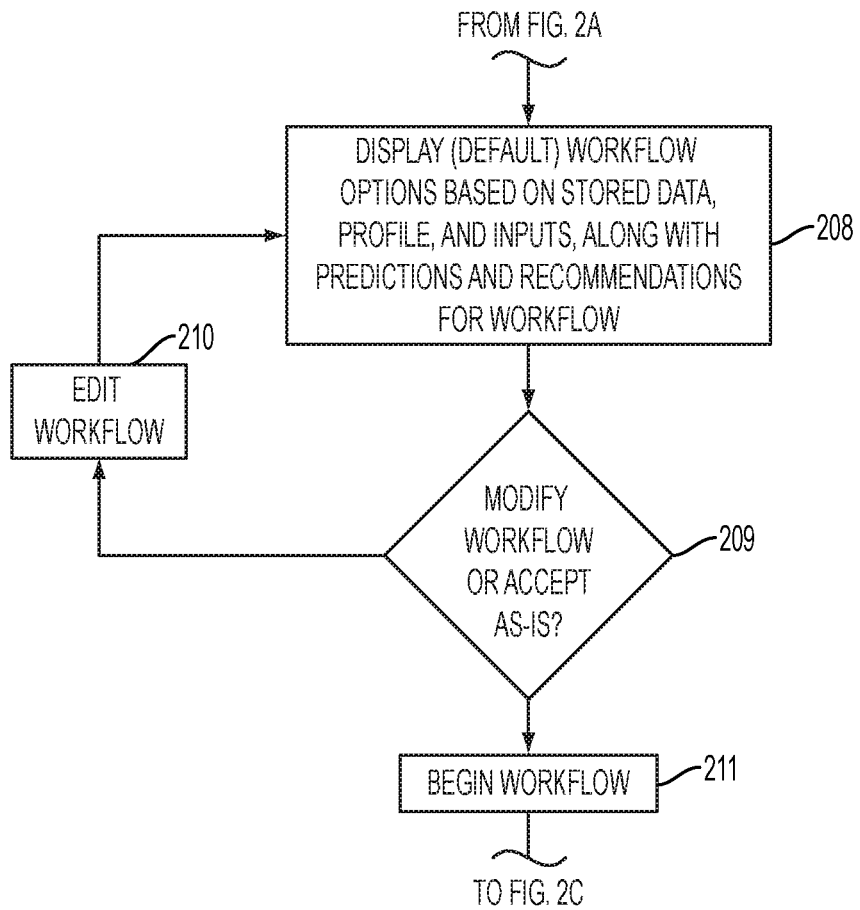
Figure 2C:
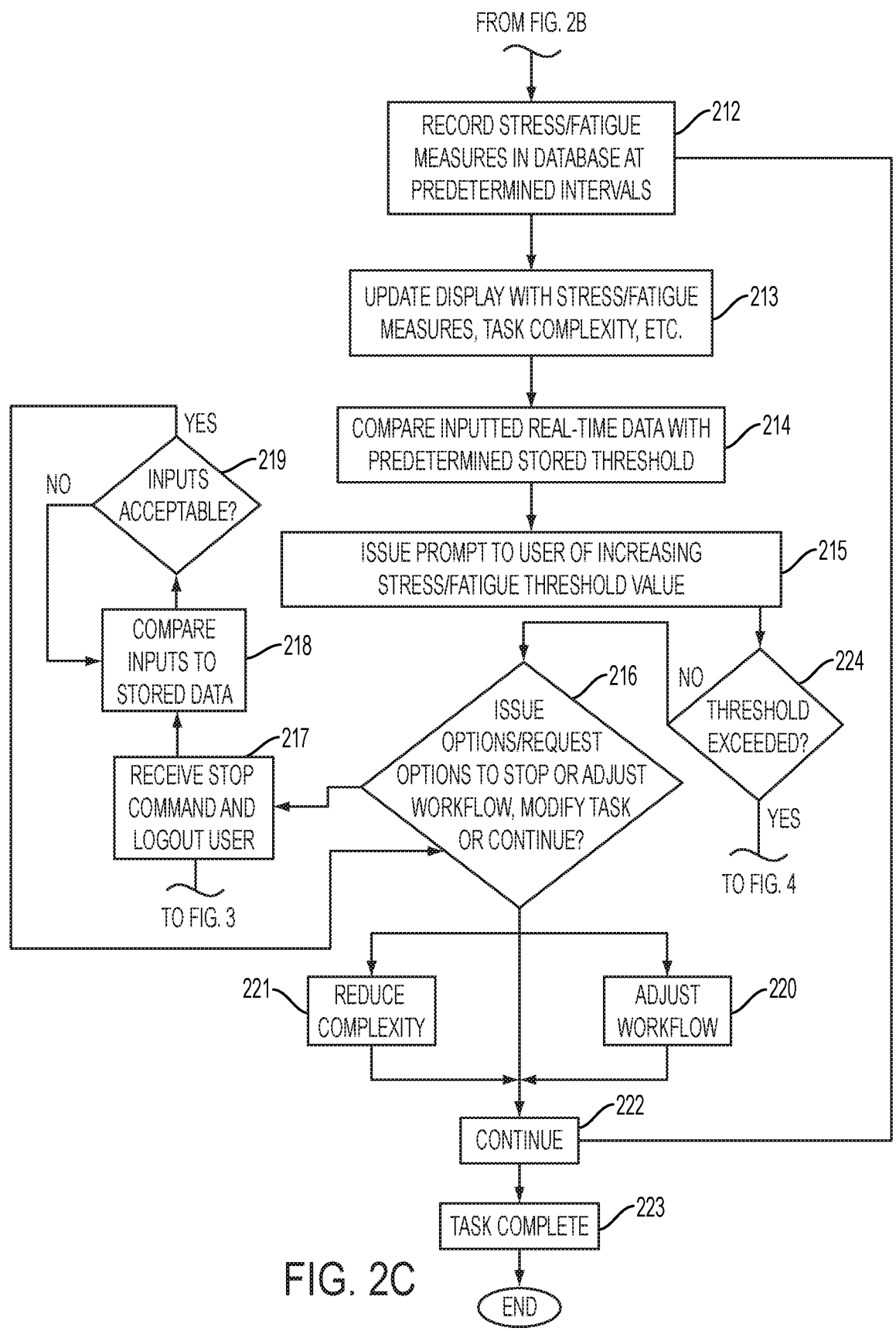

As the user works according to a particular workflow, stress/fatigue measures are taken by measurement tools 22 and recorded in the database 113, 114, 128 in step 212 (see FIG. 2B), at predetermined time intervals, by the end-user.

In step 213, the program 110 continuously updates the computer (graphical) display 102 to provide visual display of serial stress/fatigue measures, task complexity, workflow (e.g., tasks per unit time), current versus mean historical analysis, pre-defined fatigue thresholds, and anticipated rest periods, etc.

During the workflow process, the end-user can at any time highlight an area of interest on the graphical display 102 for the program 110 to provide detailed analysis.

In step 214, the program 110 compares the real-time stress/fatigue measurements being inputted into the database 113, 114, 128, with a predetermined stored threshold.

In step 215, when the inputted fatigue measurements approach the predetermined threshold, the program 110 issues an automated prompt (which is customized to end-user preferences, such as alarm, fax, email, etc.), alerting the end-user of the increasing stress and/or fatigue threshold value.

In step 216, the program 110 issues options to the end-user, in intervention, and requires instructions of:
a) stop—and the user takes a break;
b) adjust workflow (e.g., modify user interface, implement decision support tools, modify data extraction techniques, utilize automated workflow templates etc.);
c) modify task complexity (reduce complexity); or
d) continue as-is.

The user's choice dictates the next steps.

In step 217, the program 110 receives the input to stop, and the program 110 automatically logs out the user from performing any additional work (or for a predetermined period of time), with the exception of stress and fatigue measurements being available for continued input from the measurement tool(s) 22 into the database 113, 114, 128.

In step 218, during the break period, the program 110 receives inputs from the measurement tool(s) 22 into the database 113, 114, 128, of continuously assessed fatigue measurements of the user, and compares them with the stored threshold data.

In step 219, when the program's 110 comparison of the inputted fatigue data and stored fatigue threshold data, shows that the user's fatigue measurements have returned to "acceptable" levels (predetermined), then the program 110 allows the user to log in and return to work, if the user wishes that option. (Note: acceptable levels are defined by fatigue measures which fall below the predetermined fatigue threshold). If the comparison shows that acceptable levels have not been reached, then the program 110 goes back to step 218.

When the end-user returns to work, the program 110 provides the user with the options b) and c) above from step 216 (e.g., modifying workflow and task complexity), or continuing as before (option d)).

The end-user can choose options b) or c), and the program 110 will provide the end-user with a modified workflow in step 220, or reduced complexity in step 221.

Thereafter, the program 110 continues in step 222 with steps 212-215, until the task is completed in step 223, or step 216 is initiated once again.

Figure 3:
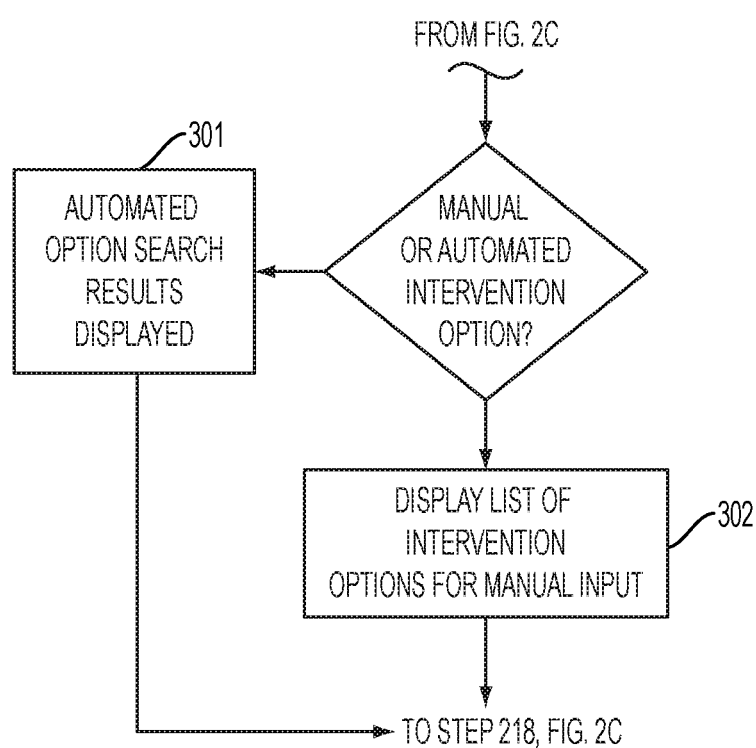
FIG. 3 is a flowchart showing steps in the intervention method of the present invention.

As an alternative to option a), after step 217 is initiated, during the break, the program 110 may present fatigue intervention options to the user for selection in step 300 (see FIG. 3). The options may include an "automated" intervention option, or a "manual" intervention option.

The user may select the "automated" option, and the program 110 will search the database 113, 114, 128 and present to the user in step 301, intervention options based upon the end-user profile, user preferences, task complexity, stress/fatigue measures recorded etc., and historical analysis of the database 113, 114, 128.

If the user selects the "manual" option, the program 110 provides the user with a list of intervention options for implementation (i.e., online games, puzzles, exercise options, etc.) in step 302.

Thereafter, as stated above, the program 110 returns to step 218.

Figure 4:
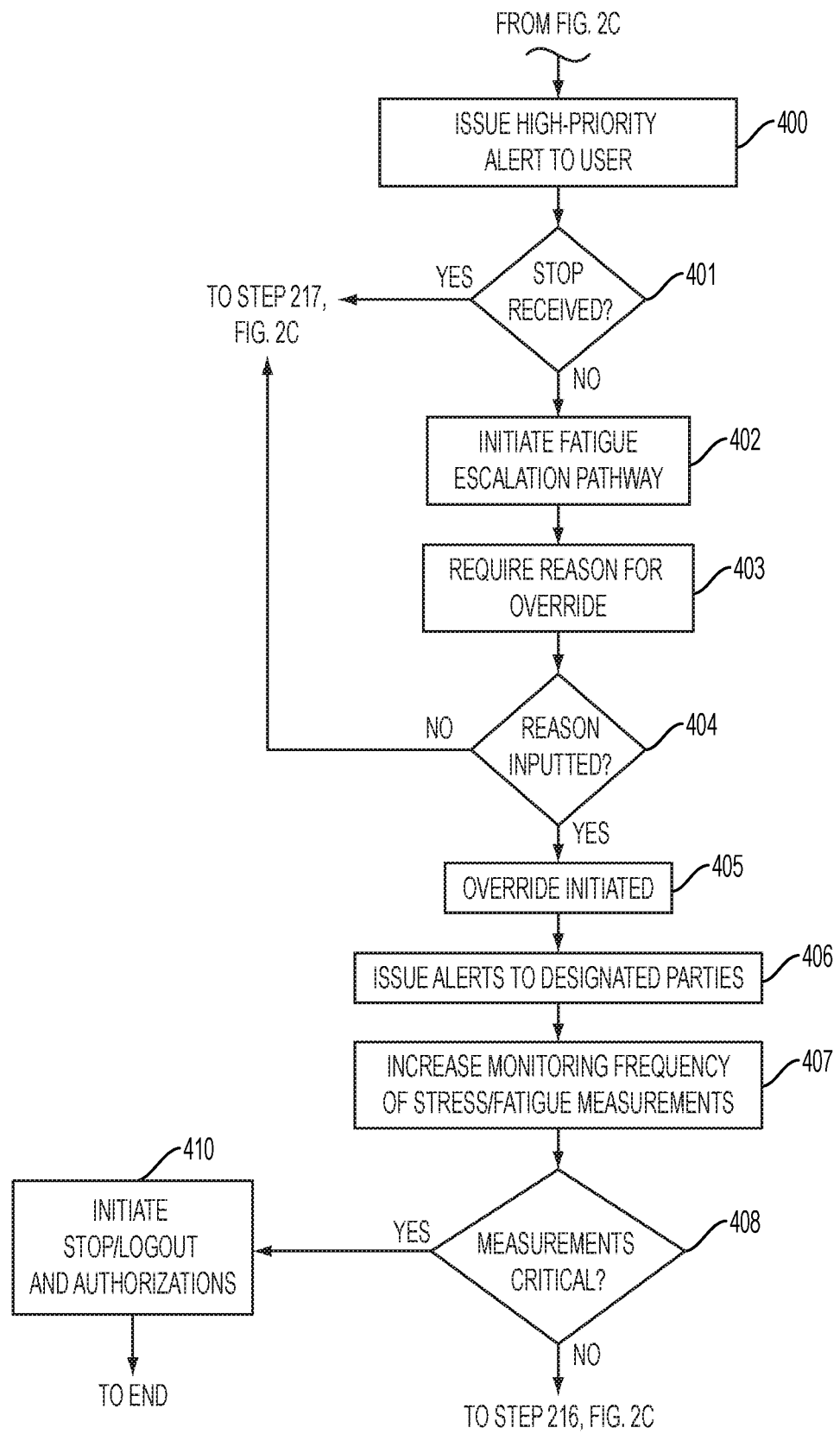
FIG. 4 is a flowchart showing steps in the intervention method of the present invention.

If the user chooses option d)—to continue working—and over time, the program 110 determines in step 224, that the predetermined fatigue threshold is exceeded, then the program 110 will issue a "high priority" alert to the end-user in step 400 (see FIG. 4). A "high-priority" alert may be an alarm at the computer 101 or the external device being used (i.e., radiographic device 21), for example.

In step 401, the user is required to proceed to step 217 in a predetermined period of time. If a stop is received, the program 110 sends the user to step 217. If not, then the program 110 will initiate a fatigue escalation pathway in step 402.

In step 403, the program 110 will require that the end-user input the reason for continuing work without workflow modification or rest. If a reason is inputted in step 405, it will initiate an override option of the program 110 taking any further steps to shut down equipment or log off the user as in steps 401/217. If no reason is inputted, the program 110 proceeds to step 217.

In step 406, the program 110 will then issue simultaneous alerts to designated parties (e.g., QA or compliance officer, hospital administrator, department chief, chief information officer (CIO)), for action.

In step 407, the program 110 will increase the monitoring frequency of the stress/fatigue measurements, with continuing, periodic prompts sent to the end-user.

In step 408, the program 110 determines whether the user's stress/fatigue measures rise above a stored predetermined "critical" threshold. If so, in step 410, the program 110 will automatically log off the user, and prevent the user's further log in or activation of any device, without authorization of the CIO, or department chief.

If the user's stress/fatigue measures do not rise above the "critical" threshold, the program 110 will proceed to step 216, and provide options for adjustment of workflow, modification of task, or simply continue as-is. The program 110 will continue monitoring in step 222, until the fatigue measures return to acceptable (i.e., below threshold) levels, the escalation pathway (400-408) is eliminated, or the task is complete in step 223.

The program 110 will initiate a verification request, where all tasks performed during the over-ride period requires secondary verification before completion. (In the case of image interpretation, for example, the examination would require over-reading by a second radiologist.)

The program 110 will refer any QA discrepancies or safety violations during the over-ride period to the institutional QA committee for review and potential disciplinary action of the user.

The radiologist workflow above illustrates one method of operation of the program 110 of the present invention, which incorporates fatigue/stress measures, database 113, 114, 128 analysis, automated feedback and prompts, and initiation of an escalation pathway in the event that important fatigue measures are recorded to the database 113, 114, 128, and no change in workflow takes place. The escalation pathway of the program 110 is designed to provide an option for the end-user to continue operation during an emergency, while providing checks and balances to ensure compliance with established standards/regulations, while maintaining appropriate QA and safety requirements.

The relationship between workflow, productivity, quality, safety, and stress/fatigue is complex and often context and user-specific. In order to accurately define the interaction effects of these variables is through prospective analysis of the database 113, 114, 128 by the program 110, which provides user and context specific data which can be correlated with quality, safety, and clinical outcomes measures. One straightforward analysis which can be performed for QA purposes, is for the program 110 to correlate documented QA and/or safety deficiencies with stress/fatigue measures at the specific date and time the task was performed.

As an example, if a QA deficiency (e.g., excessive motion artifact) occurred during the performance of a chest CT exam, the supervisory CT technologist, QA officer, or departmental administrator could easily query the database 113, 114, 128 to retrieve all data specific to the CT exam in question. In doing so, the identification of all the healthcare professionals (e.g., technologist, radiologist, ordering physician), the patient on whom the examination was performed, and the technologies used (e.g., CT scanner, image processing software, and contrast injector), are provided by the program 110. Since the QA deficiency was directly attributable to the CT technologist performing the exam, the investigating QA party could retrieve the data specific to the technologist, from the database 113, 114, 128. In the course of the program 110 performing this analysis, the technologists' time-activity curve for the date in question, would demonstrate serial fatigue measures over the course of the day, and highlight the specific time in which the CT exam in question was performed. In this example, if the program 110 identifies that fatigue measures at the time the QA deficient CT exam was performed, exceeded the pre-defined threshold, then disciplinary action and/or remedial education for the technologist in question would be required by the program 110. If on the other hand, the technologist fatigue measures at the time of CT acquisition were within normal limits, then no further action would be required by the program 110 (from the standpoint of actions related to technologist fatigue). The same type of analysis could be performed by the program 110 in the event of an adverse clinical outcome (e.g., contrast extravasation or allergic reaction to contrast), during the course of the CT exam.

An alternative QA analysis could be performed on a daily (or weekly) level by the department administrator, by automatically querying the database 113, 114, 128 for all documented QA deficiencies. The program 110 would automatically create a time-stamped printout of all fatigue measurements of the responsible parties at the specific date and time the QA deficiencies occurred. The QA derived analyses by the program 110, could easily be tailored to the individual needs of the institution or end-user, and provide valuable data for education, research, creation of best practice guidelines, and technology assessment.

The use of the program 110 as a technology assessment tool provides data-driven analysis and insight as to how different technologies contribute (or minimize) fatigue in a variety of different patterns of use and by multiple different end-users. As an example, analysis of the database 113, 114, 128 by the program 110 may show that unusually high fatigue measures are recorded for a specific technologist performing a specific exam type (e.g., CT angiography of the chest) on a specific piece of equipment (e.g., 64-detector CT scanner). Comparative analysis of other technologists at the same institution, for the same technology and exam type, by the program 110, do not corroborate increased fatigue levels. Further investigation of workflow, reveals that the technologist in question is not using the technology in the same manner of other technologists due to insufficient training. When the technologist is mentored, workflow is improved and the resulting fatigue levels (for this exam type and technology) return to baseline. This illustrates how the program's 110 analytics can be used as a combined QA and technology assessment tool. An alternative use would be comparative technology assessment (for the same task and context), which can be derived through meta-analysis of the database 113, 114, 128 by the program 110.

By standardizing the data recorded and analyzed by the program 110, multi-institutional meta-analysis can be performed, which has unlimited research potential. In addition, those institutions and individual end-users who demonstrate superior performance measures (e.g., quality, safety, workflow, productivity, and fatigue) can be identified relative to their peers, and used for creating best practice (i.e., evidence-based medicine) guidelines.

As an example, it may be determined that a specific intervention technique (or combination of variables) may provide the best results (i.e., rapid fatigue reduction) for a given context or end-user profile. Once this data has been statistically validated by the program 110, the program 110 may incorporate this intervention technique as a "stress/fatigue program recommendation", which alerts the end-user that data analysis has shown this recommendation to yield superior results for end-users of similar profiles.

While stress and fatigue have been well described as a deterrent to quality, safety, and productivity in the workplace, no single technology to date has addressed a strategy for combined diagnosis, prospective analysis, and intervention at the point of care. Medical professionals in particular are especially susceptible to occupational stress and fatigue due to increasing workflow demands, the complexity of tasks being performed, the emergent nature of practice requiring immediate and split second decisions, digitization of medical data, and prolonged shifts often resulting in insufficient sleep. The creation of standardized and objective stress and fatigue data provides an opportunity to track and analyze fatigue in real time and provide customizable interventions for improvement. The resulting stress/fatigue database 113, 114, 128, in turn, creates unique educational, research, and quality improvement applications, along with the creation of data-driven best practice guidelines.

While the present invention is applicable to a diverse number of industry applications, the medical profession is used for illustrative purposes.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A system which manages stress or fatigue in a user, comprising:
   a plurality of sensors which acquire and record physiologic metrics of a user, to measure stress or fatigue in real-time, from a user performing a workflow, the workflow including a task having a level of complexity;
   a database containing a historical baseline stress or fatigue of said user, and a threshold value of stress or fatigue of said user;
   a display; and
   a processor of a computer system which adjusts a threshold value of stress or fatigue dynamically by taking into account said historical baseline stress or fatigue of said user performing said task of said level of complexity;
   wherein said processor compares said physiologic metrics of said user with said threshold value of stress or fatigue of said user stored in said database, and notifies said user of an increase in said physiologic metrics of said user which approaches said threshold value of stress or fatigue;
   wherein said processor performs an analysis to determine whether said threshold value of stress or fatigue has been exceeded; and
   at least one interventional device, which is implemented by said processor, to provide feedback to said user that said threshold value has been exceeded, said at least one interventional device configured to change environmental conditions of a physical setting of said user, or to prevent said user from continuing said workflow on said computer system by displaying options to at least one of stop, adjust, or modify said workflow, until a reduction of stress or fatigue by said user below said predetermined threshold is determined by said processor, or said user provides a reason to override said at least one interventional device and continue said workflow.

2. The system of claim 1,
   wherein said sensors include at least one of imaging modalities, information systems technologies, image processing technology, and clinical decision support technology; and
   wherein said occupational stress assessment tool includes self-reported questionnaires.

3. The system of claim 2, wherein said processor performs at least one of assessments of end-user profiles, and scoring of said task complexity.

4. The system of claim 1, wherein said sleep quality is measured by said plurality of sensors, or a self-reported questionnaire.

5. The system of claim 4, wherein said plurality of sensors include at least one of a heart rate monitor, a blood pressure monitor, a galvanic skin response monitor, blood analyzer, brain scanner, saliva metrics, or a speech analysis monitor; and
   wherein an assessment of cognitive measures includes at least one of mathematical tasks, vigilance tasks, or repetitive reaction time tasks which are periodically introduced into the workflow of the users; and wherein said physiologic and cognitive assessment measures are continuously recorded by said processor for detection of an interval change which indicates stress or fatigue of the users.

6. The system of claim 5, wherein said analysis by said processor in order to determine said interval change is relative to stress or fatigue baselines of each of said users and context-specific baselines.

7. The system of claim 1, wherein said feedback of said interventional device is an alert, including at least one of an alarm, an email, or text, when an individual level of stress or fatigue of said user exceeds said predetermined threshold.

8. The system of claim 7, wherein said interventional device includes at least one of an environmental regulator, which changes one of a temperature, a light, or a ventilation, or a log-out mechanism of a computer.

9. The system of claim 8, wherein said interventional device includes physiological regulators including at least one of exercise, relaxation techniques, dietary, massage, aromatherapy, games, music or videos.

10. The system of claim 1,
wherein said display provides a visual display of at least one of said stress or fatigue measures, said task complexity, said user workflow, a historical analysis of user stress or fatigue, pre-defined individual user stress or fatigue thresholds, context-specific thresholds of stress or fatigue, or anticipated user rest periods.

11. The system of claim 9, wherein on condition that said individual level of stress or fatigue measured by said plurality of sensors approaches said predetermined threshold, said processor issues said alert to the user.

12. The system of claim 11, wherein in response to said alert, said user can one of stop any task, adjust said task using external or automated support, modify said task complexity, or ignore said alert and continue said task.

13. The system of claim 12, wherein when said task is stopped by said user or said processor, said plurality of sensors continue stress or fatigue measures and compares said stress or fatigue measures to said predetermined threshold, until said stress or fatigue measures fall below said predetermined threshold, at which said user can resume said task.

14. The system of claim 13, wherein when said user resumes said task, said user can resume said task with adjustments using external or automated support or modification in task complexity provided by said interventional device.

15. The system of claim 13, wherein when said task is stopped, said interventional device can initiate a partial or complete shutdown of any computer system or medical device until a review is made by authorized personnel.

16. The system of claim 13, wherein said user can override any recommendations by authorized personnel with verification by another user.

17. The system of claim 16, wherein when said task is stopped, said user can utilize stress or fatigue intervention options based upon at least one of said end-user profiles, user preferences, said task complexity, said stress or fatigue measures, or a historical analysis.

18. The system of claim 17, wherein when said user continues said task and said stress or fatigue measures continue to exceed said predetermined threshold, a fatigue escalation pathway is implemented, and said alert is issued to authorized parties for action, and a frequency of said stress or fatigue measures and issuance of alerts is increased until a critical threshold is reached at which said user is stopped from continuing said task.

19. A system which manages stress or fatigue in a user, comprising:
a plurality of sensors which acquire and record physiologic metrics of a user, to measure stress or fatigue in real-time, from a user performing a workflow, the workflow including a task having a level of complexity;
a database containing a historical baseline stress or fatigue of said user, and a threshold value of stress or fatigue of said user;
a display; and
a processor of a computer system which adjusts a threshold value of stress or fatigue dynamically by taking into account said historical baseline stress or fatigue of said user performing said task of said level of complexity;
wherein said processor compares said physiologic metrics of said user with said threshold value of stress or fatigue of said user stored in said database, and notifies said user of an increase in said physiologic metrics of said user which approaches said threshold value of stress or fatigue;
wherein said processor performs an analysis to determine whether said threshold value of stress or fatigue has been exceeded; and
at least one interventional device, which is implemented by said processor, to provide feedback to said user that said threshold value has been exceeded, said at least one interventional device configured to change environmental conditions of a physical setting of said user.

* * * * *